(12) United States Patent
Palti-Wasserman et al.

(10) Patent No.: US 7,326,938 B2
(45) Date of Patent: Feb. 5, 2008

(54) OPTICAL SYSTEM AND METHOD FOR INSPECTING FLUORESCENTLY LABELED BIOLOGICAL SPECIMENS

(75) Inventors: Daphna Palti-Wasserman, Haifa (IL); Yaron Kober, Alona (IL); Erez Kelly, Modean (IL)

(73) Assignee: D.N.R. Imaging Systems Ltd., Haifa (IL)

( * ) Notice: Subject to any disclaimer, the term of this patent is extended or adjusted under 35 U.S.C. 154(b) by 143 days.

(21) Appl. No.: 10/487,441

(22) PCT Filed: Jul. 30, 2002

(86) PCT No.: PCT/IL02/00625

§ 371 (c)(1),
(2), (4) Date: Apr. 6, 2005

(87) PCT Pub. No.: WO03/019161

PCT Pub. Date: Mar. 6, 2003

(65) Prior Publication Data

US 2005/0179899 A1 Aug. 18, 2005

Related U.S. Application Data

(60) Provisional application No. 60/314,116, filed on Aug. 23, 2001.

(51) Int. Cl.
*G01N 21/64* (2006.01)

(52) U.S. Cl. .................................. 250/461.2; 359/395
(58) Field of Classification Search ............. 250/461.2; 359/395
See application file for complete search history.

(56) References Cited

U.S. PATENT DOCUMENTS

| 5,436,718 | A | 7/1995 | Fernandes et al. |
| 5,774,214 | A | 6/1998 | Prettyjohns |
| 6,226,392 | B1 | 5/2001 | Bacus et al. |
| 6,252,236 | B1 | 6/2001 | Trulson et al. |
| 6,545,264 | B1 * | 4/2003 | Stern .......................... 250/234 |

FOREIGN PATENT DOCUMENTS

EP 0990889 A1 4/2000

* cited by examiner

*Primary Examiner*—David Porta
*Assistant Examiner*—Djura Malevic
(74) *Attorney, Agent, or Firm*—Browdy and Neimark, PLLC

(57) ABSTRACT

A system for imaging a fluorescently labeled sample is presented, The system comprises a capsule, which is a closable structure made of a material isolating the inside of the capsule from its surrounding environment, and which has a support stage for receiving the sample and carrying it thereinside during the imaging; and an optical device at least partly accommodated inside the capsule and operable to illuminate the sample with incident radiation to excite a fluorescent response of the sample, detect the fluorescent response, and generate data indicative thereof.

25 Claims, 3 Drawing Sheets

OPTICAL SYSTEM AND METHOD FOR INSPECTING FLUORESCENTLY LABELED BIOLOGICAL SPECIMENS

FIELD OF THE INVENTION

This invention is generally in the field of optical measurement/inspection techniques and relates to an optical system and method for inspecting fluorescently labeled biological specimens.

BACKGROUND OF THE INVENTION

One of the new emerging techniques used today in the research of molecular biology and genetics is fluorescent labeling of a biological specimen. According to this technique, fluorescent probes are used to mark the specific locations in a biological specimen aimed at detecting different genes, chromosomes, DNA strands, proteins, and bacteria.

In recent years, the fluorescent labeling based techniques have started to push their way into the diagnostic world, and it is anticipated that in the near future diagnostic assays based on fluorescent labeling will be used more and more routinely.

According to conventional techniques, the detection of fluorescent probes is done in research laboratories by using an "off the shelf" fluorescent microscope. The use of a fluorescent microscope was a logical choice, since this machine was readily available in most research labs. Furthermore, it was a familiar tool to all researchers, and had the benefit of being a multi purpose platform used for other lab applications as well.

However, the detection of fluorescent probes in a biological sample by means of the conventional fluorescent microscope suffers from several drawbacks associated with the following. Today, in diagnostic laboratories that use fluorescent techniques, an operator with genetic training typically manually operates a fluorescent microscope. The operator must manually select the correct objective and filters, manually scan the slide and search for good genetic material, focus on each image, analyze the fluorescent signals, and write down his analysis. The operator has to look through a binocular eyepiece during the entire process, which is a cumbersome and tiring process. Thus, an operator cannot work on the microscope for more than a few hours continuously, and not more than 8-10 hours daily. This of course limits the number of tests a lab can perform, thus limiting the lab's throughput significantly.

Furthermore, the laboratory, where this analysis is done, has to be in blackout conditions. This is associated with one of the major problems of using fluorescent labeling for routine diagnostic assays, consisting of keeping the fluorescent labeling "alive" long enough to finish the entire procedure, which typically includes scanning the sample on a slide, looking for region of interests (ROIs) in the sample (for example, a nucleus of the cell or a chromosome), focusing on the ROIs, taking an image thereof, refocusing on sub areas within the ROI (for example labeled genes), and taking images of the these sub areas as well. This procedure takes quite a while, since a large number of ROIs must be considered to achieve the high reliability required from an assay used for diagnostic purposes. For example, in prenatal FISH tests (fluorescence in situ hybridization) at least 100 good regions of interest (nuclei) are needed to be imaged for giving a reliable diagnosis from the test ("Prenatal diagnosis using interphase fluorescence in situ hybridization (FISH)", Prenat Diagn 2001; 21: 293-301. DOI: 10.1002/p. 57). FISH method is typically used to detect the absence or excess of a specific gene (e.g., elastin gene) from a chromosome, e.g., to detect the presence of down syndrome.

To detect 100 good enough regions of interest, one must scan several hundreds of fields on the sample. Working for so long on the sample raises the problem of bleaching. Bleaching of a sample causes the fluorescent probes to fade, thus making the reading of the sample impossible. This phenomenon, which occurs within minutes, is stimulated by light and oxygen. Operation with the conventional fluorescent microscope thus requires operation in the dark, and implies that other activities requiring light cannot be carried out at the same time and place, when fluorescent analysis is in process. As a result, all laboratory work has to be halted when fluorescent signals are analyzed, or a separate room has to be assigned for the fluorescent microscope. Furthermore, the necessity to work in a dark environment, affects the performance of the microscope operator. Working in the dark, is no doubt, a cumbersome task.

Other environmental hazards of the conventional techniques, such as heat, humidity, radiation, electromagnetic waves, also have undesired influence on some biological samples. With the conventional microscope and conventional technique, operating personnel are exposed to safety hazards due to UV light typically used to excite the fluorescent sample, but is harmful to people.

The use of a "semi-automatic" fluorescent microscope set-up has been proposed (BX51 Epi-Fluorescence Microscope commercially available from Olympus). In this set-up, a digital camera and a computer are added to the fluorescent microscope solely for archiving the images so as to enable reviewing the images at a later time. An "automatic" fluorescent microscope set-up (DM RXA2 Fluorescence Microscope commercially available from Leica) allows for integrating the "off-the-shelf" components such as a microscope, digital camera, scanning stage, and computer, in conjunction with a software package that controls the operation of these components. However, using the "off-the-shelf" components that were not designed specifically for fluorescent diagnostic tasks (to comply with the demands of the fluorescent-based diagnostic world) obviously decreases performance and increases costs of the optical system.

SUMMARY OF THE INVENTION

The use of fluorescent probes routinely for diagnostic purposes creates new standards and demands for a fluorescent detection system. Such a system must provide a complete and full solution for a fluorescent-based diagnosis. The system must be characterized by a high throughput capability, high levels of automation, a simple graphic user interface (GUI) that enables minimal user operating mistakes and thereby allows for layman operation of the system, a high level of reliability and accuracy, and last but not least, it must be economically beneficial.

The main idea of the present invention consists of solving the above problems by the encapsulation of a stage intended for supporting a fluorescently labeled sample under inspection, and an optical inspection (imaging) system. Such a capsule is made of a material preventing the penetration of light into the capsule from the outside thereof (i.e., non-transparent material), and preferably also preventing the penetration of electromagnetic waves (i.e., electrically conductive material). The capsule preferably also includes one or more environment control sensors, and is equipped with means enabling the adjustment of the corresponding environment conditions inside the capsule so as to meet the requirements of an optical inspection of fluorescently labeled samples.

The technique of the present invention thus provides a unique platform that complies with the new demands arising from turning the latest research techniques in fluorescence into tomorrow's diagnostic tools. The system and method of the present invention makes up a Fluorescent Working Station (F-WOS) constructed and operated to provide optimal conditions for acquiring high-end fluorescent images (i.e., the combination of low light sensing, small size and high magnification, together with the enhanced image processing and control) from biological samples for research and diagnostic tasks, and to provide optimal conditions for the sample, fluorescent signals, operator, and all other personal working in the lab. By designing a complete system especially for fluorescent diagnostics, the high performance, high throughput, and low price system is obtained. It should be noted that fluorescent signals, for diagnostic tasks, are characterized by a low light (about 0.001 lux), capability of detecting small size fluorescent labels (0.1-0.4 microns), fast fluorescent intensity decay with time (bleaching), and environmental sensitivity. This means that in fluorescent imaging, working on the "edge" of technology is required, and it is thus crucial to address the fluorescent signal quality issues, as well as the imaging quality issues, for obtaining the best results.

The F-WOS of the present invention is the first fluorescent-based system that makes a significant effort in improving the quality of the fluorescent signals, and not just improving the quality of the acquired images. The F-WOS enables to easily load a fluorescent slide into the capsule, automatic scanning of the slide in the X,Y,Z planes at the appropriate resolution and speed, searching for the designated regions of interest on the fly, and optimal acquisition of the required images for research and diagnosis needs.

According to one aspect of the present invention, there is provided a system for imaging a fluorescently labeled sample, the system comprising a capsule, which is a closable structure made of a material isolating the inside of the capsule from its surrounding environment, and which has a support stage for receiving the sample and carrying it thereinside during the imaging; and an optical device at least partly accommodated inside the capsule and operable to illuminate the sample with incident radiation to excite a fluorescent response of the sample, detect the fluorescent response, and generate data indicative thereof.

Preferably, the capsule comprises one or more sensors for sensing the environment condition(s) inside the capsule to be controlled, and inlet and outlet means enabling to desirably affect the corresponding condition(s) inside the capsule. The capsule thus presents a "controlled environmental capsule" (CEC). The sensors suitable to be used in the capsule include at least one of the following: a temperature sensor, an ambient light sensor, an electromagnetic radiation sensor, oxygen or other gases' sensor, and a humidity sensor. The CEC is designed to protect the biological media and the fluorescent probes therein from environmental hazards, and to provide them with optimal conditions during the imaging. For example, the capsule protects the sample from unwanted light in the room, high temperature, and the presence of oxygen, causing the sample to fade quickly (the Bleaching phenomena). Providing these optimal conditions for the fluorescent sample improves the quality of the fluorescent signals. The CEC also provides protection for the operating personal from hazardous conditions of the system such as the use of UV light. Furthermore, the encapsulation of the sample with the optical device enables installation of the working station in any room or laboratory, without the necessity to darken the room when working with the fluorescent signals, thus stopping all other activities in the laboratory at that time.

The optical device provides: means for selecting and guiding the excitation light to the sample, means for collecting and selecting the desired emitted (excited) light from the sample, means for forming the fluorescent image at a selected focal plane, and preferably also means for enlarging the images. All components are designed to obtain the best fluorescent images possible.

The optical device thus includes a light source system, an image formation system, and light directing/collecting optics. The light source uses one or more light sources of the kind generating excitation incident radiation to excite a fluorescent response of the sample. The optics used may include a light guiding means (filters) for selecting and guiding the desired excitation light to the sample, a beam shaping optics in the optical path of the exciting light, a light collecting optics for collecting light coming from the sample and selecting therefrom the desired fluorescent light, and an imaging optics to form the fluorescent image of the sample. The detection unit may include one or more detectors (e.g., with different specifications). For example, the detection unit may include a single imaging detector, but preferably includes at least two such detectors with different attributes. For example, one detector is a self-designed CMOS camera aimed at identifying pre-defined ROI(s) on-the-fly (in real time) and processing the images on the camera chip itself, thereby saving the need to send the images to an external computer, and the other detector is a cooled CCD camera aimed at providing high quality images for analysis and acquisition.

The device further includes a scanning system, which enables scanning the sample at different resolution and speeds at the X, Y and Z directions (3D scanning). The scanning system supports the ROI search and identification, preferably utilizing also auto-focusing abilities, and provides the F-WOS with the ability to automatically detect a large amount of fluorescent signals in a short period of time.

The system of the present invention utilizes a control unit (Computerized Central Control) that automatically controls and synchronizes the operation of the entire workstation). The control unit receives data from data indicative of the detected fluorescent response from the detector(s) to generate data indicative of an image of the sample, and preferably also receives data indicative of the environment condition(s) inside the capsule to analyze this data and operate the inlet and output channels of the system accordingly. The control unit is typically a computer device connectable to the capsule through wires or wireless communication, and includes inter alia a database utility for storing a specifically designed database, a data processing and analyzing utility preprogrammed with specially designed algorithms, and a display unit. The control unit preferably comprises appropriate communication means enabling "downloading" of the acquired images and all relevant data to the database. The algorithm packages especially designed for use in the F-WOS are responsible inter alia for the following: finding predefined regions of interest (ROI), focusing on these regions, analyzing the images in the ROI, selecting sub areas in the ROI for further acquiring and analysis, calculating the optimal parameters (i.e. roundness, overlapping, size and some others) for acquiring the different images, and giving a diagnosis evaluation based on the acquired images and predefined statistics. The same or an additional control unit is operable to automatically control and synchronize the operation of the entire workstation. The database utility enables the following operations: saving the acquired images, saving all other relevant information, conducting different search algorithms on the database, and options for adding new fields of data to each item in the database.

The fluorescent sample may be of the kind prepared in the FISH method, and may be used for obtaining diagnostic results, e.g., by using Aneuploidy methods.

According to another aspect of the present invention, there is provided an optical system for imaging a fluorescently labeled sample, the system comprising:

a capsule, which is a closable structure made of a material isolating the inside of the capsule from surrounding environment, the capsule comprising a support stage for receiving the sample and carrying it thereinside during the imaging process in a manner enabling displacement of the sample with respect to an inspection plane, and having inlet and output channels operable to affect environment conditions inside the capsule;

an optical device at least partly accommodated inside the capsule and operable to illuminate the sample with incident exciting radiation to excite a fluorescent response of the sample, detect the fluorescent response, and generate data indicative thereof;

a sensor panel accommodated inside the capsule and operable to detect at least one of the following environmental conditions inside the capsule: temperature, light intensity, electromagnetic radiation intensity, content of oxygen or other gases, and humidity; and to generate data indicative thereof; and a control unit connectable to the capsule and response to said data indicative of the detected fluorescent response to output an image of the illuminated region of the sample, responsive to said data indicative of the at least one environmental condition to operate the inlet and output channels of the capsule so as to provide a desired environment condition inside the capsule.

According to yet another embodiment of the invention, there is provided a method of imaging a fluorescently labeled sample utilizing the above system, the method comprising:

(i) first scanning of the sample to detect regions of interest in the sample and determine coordinates of the detected regions of interest;

(ii) utilizing the results of the first scanning, and performing second scanning of the regions of interest to detect sub-areas of the regions of interest containing the fluorescent labels and acquire images of said sub-areas.

The first scanning is performed at low oxygen level in the capsule as compared to that of environment outside the capsule, and relatively low temperature of the sample as compared to that of the second scanning.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
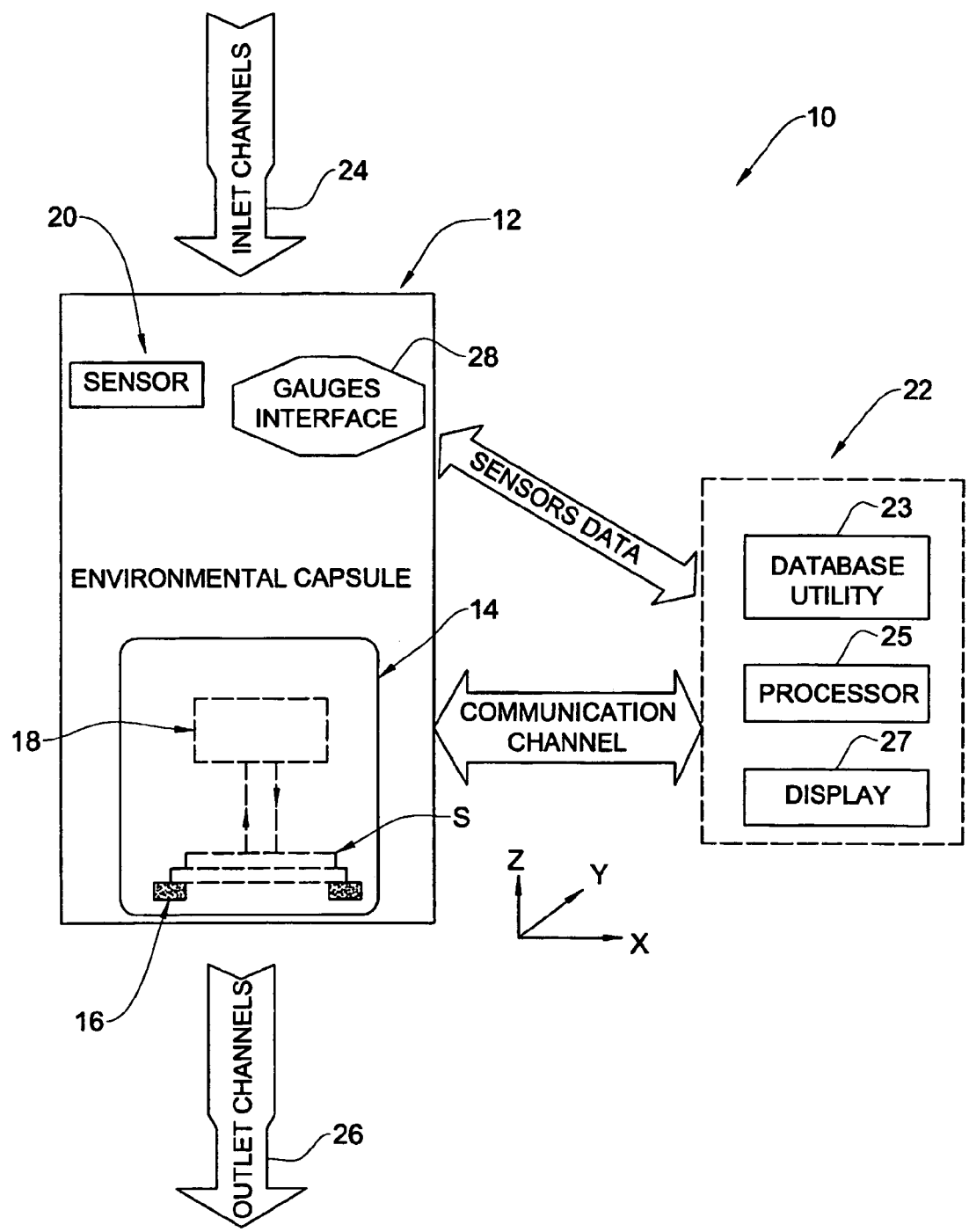
FIG. 1 is a schematic illustration of a fluorescent optical system according to the invention.

Referring to FIG. 1, there is schematically illustrated an optical system 10 according to the invention for imaging fluorescently labeled samples. The system 10 comprises a control environment capsule (CEC) 12 that is formed with a door 14 for receiving a sample-on-slide S and includes a stage 16 for supporting the sample S during the system operation, and an optical device 18. The sample is a biological specimen that should be prevented from being illuminated all the time except for that needed for imaging the sample. To this end, the sample-on-slide may be stored in a "pre-loading" cassette designed for carrying a single slide or multiple slides in darkness. The slide can be manually loaded onto the stage 16, or automatically by means of a robot. This can be implemented by an automatic movement of the stage 16 into a loading position when the door 14 is opened. If the slide in cassette is used, the cassette can be formed with a shiftable cover that is automatically shifted into its open position, when the system is put in operation.

The optical device 18 comprises an excitation light system, an image formation (detection) system, and light directing/collecting optics, as will be described more specifically further below with reference to FIG. 2. In the present example, all these elements of the optical device are located inside the capsule 12, but it should be understood that either the light source or detector(s) or both may be located outside the capsule and light may be guided towards and/or away from these elements using optical path or fibers.

The CEC 12 preferably also has a sensor arrangement (e.g., sensor panel) 20 including one or more sensors capable of measuring the current environment condition(s) in the capsule. The sensor arrangement 20 may include, for example, light sensors, oxygen sensor, temperature sensor, humidity sensor, and a pressure sensor.

Connectable to the system 10 (through wires or wireless) is a control unit 22 that operates the system and processes data indicative of images of the sample.

The CEC 12 is a closed chamber made of non-transparent electrically conductive material (e.g., metal), which isolates the sample from all undesired conditions such as light, air, electro-magnetic radiation, temperature, and humidity, and has inlet and outlet channels 24 and 26 through which the environment condition(s) inside the CEC can be appropriately adjusted. The inlet channels 24 are responsible for entering matter to the CEC to balance the environment. For example, cooled air can be entered through the inlet channels to thereby lower the temperature in the capsule, when a temperature level higher than a desired one is detected via a respective sensor. The outlet channels 26 are responsible for drawing out matter from the capsule environment. For example, drawing out air through the channel 26 and entering nitrogen through the inlet cannel 24 would cause lowering of the oxygen content in the capsule.

The sample-on-slide S is loaded into the chamber through the door 14, and put into its inspection position on the support stage 16. The latter is driven by a suitable drive (not shown) for movement along the X, Y, and Z axes. It should be understood that in the present example of the invention, where auto-focusing is implemented as a passive mathematical procedure utilizing grabbing of several pictures along the Z-axis, and then calculated the focal position, the stage 16 is the only movable element. Generally, however, any other suitable auto-focusing technique can be used utilizing the Z-movement of an objective lens. Prior to loading the sample into the CEC, the desired environment inside the CEC is set. This can be done using a gauges interface 28 or from the control unit 22. It should be noted that the gauges interface can be part of the CEC, of the control unit 22, or can be a separate unit connectable to the CEC and to the control unit 22. The control unit 22 has a database utility 23, a data processing and analyzing utility 25, and a display utility 27. It should be noted that, generally, the database utility can be part of another external device connectable to the control unit. Preset environmental conditions, which are optimal for a specific sample under inspection, may be automatically loaded from the database utility. In other cases, manual setting of the environmental parameters may be desired. The environmental data generated by the sensor(s) 20 is transferred to the control unit 22 via a communication channel (wire-based or wireless), and is processed by comparing this data to the set parameters. The desired environment is then obtained by controlling the inlet and outlet channels 24 and 26 in a closed loop with feedback readings from the sensors 20 or in an open loop (by manual operation of the inlet and outlet channels. For example, if due to some light heat the temperature in the capsule is changed, the respective sensor feels this change, and generates a signal to the control unit thereby initiating a cooling procedure, until the temperature reaches the desired level.

Figure 2:
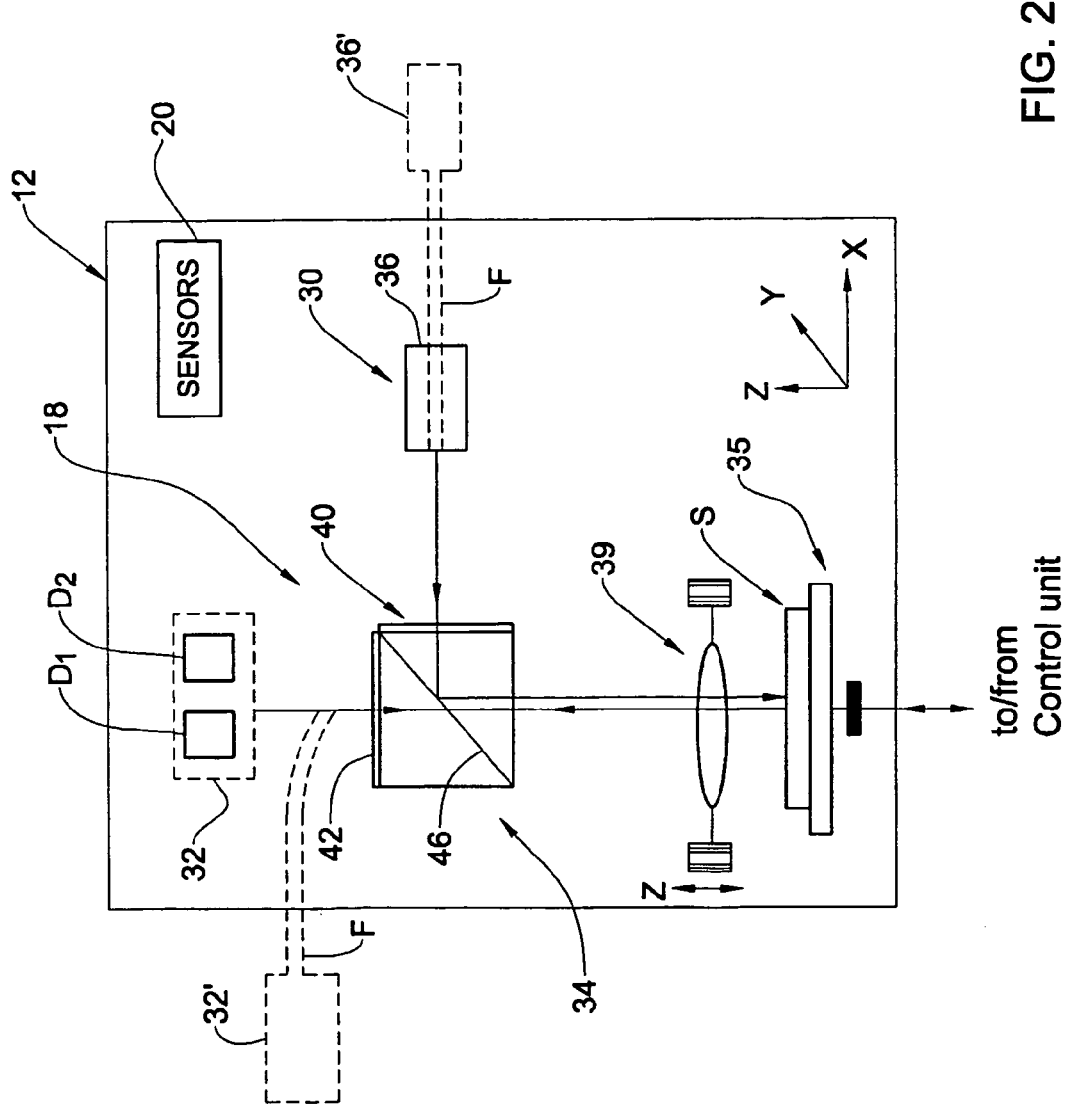
FIG. 2 more specifically illustrates as optical device suitable to be used in the system of FIG. 1.

FIG. 2 more specifically illustrates the optical device 18. The device 18 comprises an excitation light source system 30; an image formation system 32 including a detector unit; a light directing/collecting optics 34; and a scanning system 35. As shown in the figure in dashed lines, the light source 36' and a detector unit 32' (or one of them) can be located outside the CEC, in which case light is guided through optical path or fibers F. Generally, the system of the present invention can utilize the conventional fluorescent microscope modified by placing at least its light directing/collecting optics into the CEC equipped with a sensor arrangement and inlet and outlet channels.

The sample is a biological specimen having fluorescent labels. Accordingly, the excitation light system 30 includes a light source 36 of the kind generating light including a wavelength range $\lambda_1$ capable of exciting a fluorescent response $\lambda_2$ of the sample. Such a light source may be of any suitable type for fluorescent imaging, for example, a Mercury light source, a Xenon light source, a laser-based light source generating light of UV, Visible, or IR, or a combination of these light sources. The light source system may include: a single light source emitting light of a desired spectrum capable of exciting a fluorescent response of the sample, a single broadband light source associated with one or more spectral filters for selectively separating a desired exciting component from the emitted light, or more than one light source of different spectral ranges or of the same spectral range, each associated with an spectral filter.

The light directing/collecting optics 34 typically includes an objective lens arrangement 39, which is preferably used for both focusing the incident exciting beam onto the sample and collecting light returned from the sample. As shown, in the present example, the light directing/collecting optics utilizes a light filtering assembly 40 accommodated in the illumination channel, namely, in the optical path of light generated by the light source system. The assembly 40 is designed to select the desired wavelength for the excitation light. Several different filters can be located on a wheel or a slider, so they can be easily changed within and between applications. This configuration gives the system the ability to easily handle many different fluorescent applications. The filtering arrangement preferably comprises a further filter assembly 42 in the detection channel, namely, in the optical path of light propagating towards a detector to enable detection of the desired wavelength. Similarly, the filters may be located on a wheel or a slider, so they can be easily changed within and between applications, to thereby allow for handling many different fluorescent applications. The image formation system uses the objective lens arrangement 39 to form from the selected fluorescent light an image of a desired size on a predefined focal plain of the lenses. This stage is important, when infinity optics is used along the optical path.

In the preferred embodiment of the invention, the excitation and image formation systems operate in the epifluorescent fashion. In this case, the microscope objective (generally, focusing optics) 39 is used for guiding the exciting light $\lambda_1$ to the sample as well as for collecting the emitted fluorescent light $\lambda_2$ from the sample, and enlarging it. To this end, a dichroic mirror 46 is used to spatially separate between the excitation and excited light and direct them along the illumination and detection channels, respectively. The mirror 46 and the filter assemblies 40 and 42 can be arranged as a common filter cube. The use of epi-illumination conditions eliminates the need for a transparent slide.

The image formation system 32 is designed for replacing the viewing of the image by a human eye at the focal plain. A light detector arrangement is used to automatically capture the images instead of the human observer. An algorithm, which calculates the best parameters for each image, is used for this procedure. Generally, a single detector (CCD or CMOS camera) can be used for the purposes of the present invention, but preferably the detection system uses multiple light detectors (preferably two or three such detectors). In this case, each light detector can be of a different type, thus providing different attributes to the detected images. The detectors may differ in resolution, sensitivity, noise, and the overall image quality they give. In one specific embodiment of the invention exemplified in FIG. 2, the image formation system 32 includes two light detectors $D_1$ and $D_2$. Detector $D_1$ is a high performance detector, preferably CCD camera (generally, CMOS can be used as well), which is used for catching the fine details of the image. A high-performance cooled CCD camera is capable of delivering quality low light, high-resolution images. The other detector $D_2$ is preferably a CMOS camera (or CCD) is used to provide fast images for evaluating the focus plane and detecting regions of interest "on the fly" (i.e., regions having fluorescent singles or labels) This second detector $D_2$ (CMOS camera) also provides the system with fast hardware components that can perform some image processing on-the-fly, without the need to transfer the entire image to the computer. The two detectors are thus used for, respectively, rough estimation of the ROI, and detecting and analyzing the fluorescent signals (labels) themselves in sub-areas of ROIs (which requires higher magnification).

The scanning system 35 includes a drive mechanism for moving the stage with a sample-on-slide in the X-Y plane (inspection plane) and along the Z-axis. The scanning system is appropriately operated by the control unit to enable a 3-D search, looking for relevant predefined information on the fluorescent sample. The search is conducted by moving the sample (stage) in the x, y, and z directions at different resolutions and speeds, and searching for predefined objects. In the F-WOS system, the predefined objects are cell nucleus, chromosomes, or specific labeled genes. The scanning system follows a predefined search route, and saves the search results, which include the presence of the searched object, i.e., region of interest, as well as its exact coordinates. The system is also capable of returning accurately to the certain ROI using the saved coordinates. The searching speed, resolution, path, and objective location are calculated, using predefined information specifying the sample type, and special algorithms. The entire search is supported by advanced image processing algorithms in both hardware and software. The scanning system provides the F-WOS with the ability to automatically detect and acquire a large amount of fluorescent signals in a short period of time.

Turning back to FIG. 1, the control unit 22 operates to provide automatic monitoring, controlling and synchronizing of the operations of all functional elements of the system 10 (working station). The control unit enables to load pre-set programs for scanning in a predefined manner according to a specific application, as well as to easily program the station for new scanning modes and applications. The communication between the system 10 and the control unit 22 provides for the continuous flow of data and information from the different stages of the system to the control unit and back from it to the different stages of the system. All the acquired images as well as the system parameters and other selected parameters (such as exposure time, gain, sample's initial location, coloring materials, etc.) are transferred to the control unit 22 via the communication channels that can be wired channels utilizing any of the known protocols for image and data transfer (such as "FireWire"), or can be wireless communication channels utilizing broadcasting techniques to transfer the information to the control unit and back (for example the known BlueTooth technology). As indicated above, the control unit has the data processing and analyzing utility preprogrammed with specially designed algorithms for the FWOS. These algorithms are responsible inter alia for the following functions: finding predefined regions of interest (ROI), analyzing the images in the ROI, selecting sub-areas in the ROI for further acquiring and analysis, calculating the optimal parameters (i.e. roundness, overlapping, size and some others) for acquiring the different images, selecting the best configuration for the light source, calculating the preferred optical path for the sample, and providing a diagnostic evaluation based on the acquired images and predefined statistics.

The database utility 23 is designed to enable the following functions: saving the acquired images as well as all other relevant information including among other things: all systems parameters, slide (sample) information, patient information, and analysis results. The control unit also offers advanced search algorithms to use on the database utility on both images and data, and an easy option for adding new fields of data to the database. The Database can be local one—physically residing on the control unit, or it can be physically in a far way location. Access to a central database can be through the Internet or any other type of net. Since the database includes sensitive information, it must include some kind of security facilities (personal key or password) providing authorization control in both writing and reading from the database. Since the F-WOS system of the present invention is intended for use in hospital labs, the database format is compatible with other computerized databases in the hospital.

It is important to note that the system of the present invention provides for an improved GUI of the system. Basically, the operation of the system is carried out from the control unit 22 (e.g., personal computer). The operator will first have to identify himself and enter the ID of the sample. Then, he will be able to select the name of the fluorescent dye used for labeling the sample, or the fluorescent diagnostic kit used from a set of preset programs, thus defining the sample type. Based on this information, the system will be able to set all its parameters automatically and start operating. The selection of all parameters includes the selection of the correct objective, filters, scan type, resolution, image acquisition parameters, temperature, light intensity, scanning route, etc. When a new fluorescent dye is used, the user can manually set these parameters from the GUI, and from that point the system operates automatically. After all images are acquired, the operator can view the images as an image gallery on the monitor of the control unit. Using the image gallery tools, the operator can easily and quickly view all images, and complete the diagnostic procedure.

Figure 3:
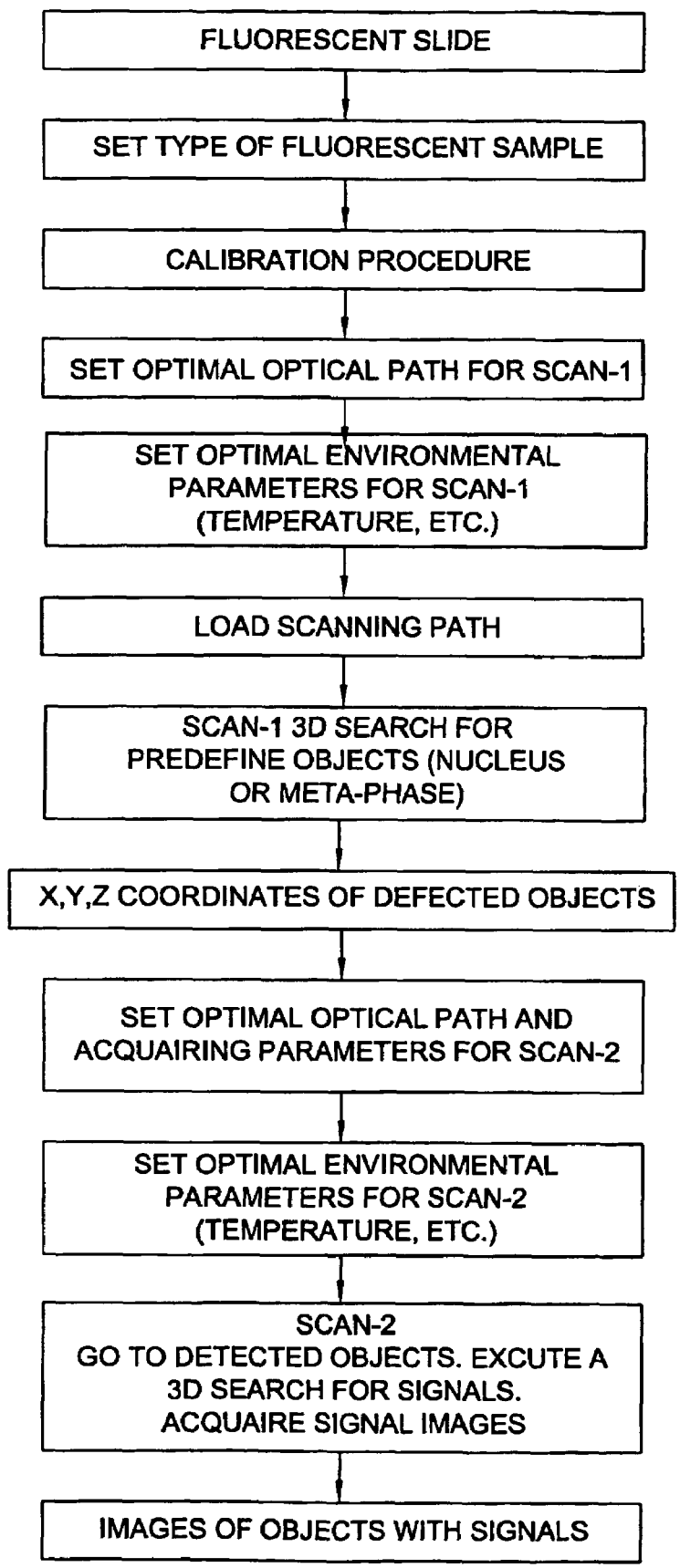
FIG. 3 exemplifies a flow diagram of the operational steps of a method according to the invention.

The system operation thus starts with setting the desired environment inside the CEC, and loading a fluorescent sample-on-slide into the CEC. Then, the sample type is set. To this end, the operator enters all relevant information (slide ID, operator ID etc.) and sets the sample's type, either by selecting it from a pre-set menu or by setting it manually. The process ends, when a complete set of digital images is stored in the database facility for further analysis. To achieve this, the system utilizes a two-step scanning scheme. This scheme will now be described with reference to FIG. 3.

A fluorescently labeled sample is entered into the system (i.e., into the capsule), and the sample's type is set. Then, a calibration process based on the input parameters is executed. During this process, a set of images is acquired under different conditions such as light intensity, filter type, and Z-axis position. From this process, the optimal parameters are chosen. For example, the optimal light source intensity is determined as that corresponding to an optimum between the maximum fluorescent emission of the sample obtained at the minimum bleaching. Using the calibration results and all a priori information entered to the system, all optical parameters, such as objective, light source intensity, filters, optics, are set automatically for the first scan. To enable optimizing of the results of the first scan, all environmental parameters (e.g., temperature, oxygen level) are also set. For the first scan, a low temperature (about 2-8 centigrade, i.e., substantially frozen or slightly heated sample) and low oxygen level (as compared to that of the environment outside the CEC) is used. For the entire system operation (i.e., the first and second scans), dark environment inside the CEC (for example, less then 0.001 lux) is set and kept, except for the time period of the light source operation). The calibration results and all a priori information entered into the system are also used to calculate the route of the scanning process, such as to provide the desired images in minimum time, with minimum bleaching.

The first scan consists of a quick screening of the slide's content, so as to identify the ROIs as quickly as possible, with minimum bleaching to the sample. The ROIs are those regions in the sample that contain cell nuclei or chromosomes during the Meta-Phase (i.e., containing fluorescent labels and preferably of a desired size and roundness). Also determined in the first scan is overlapping between the adjacent ROIs, so as to take this information into account for further data analysis. For this screening process, a 3-D search is conducted on the slide (sample). Since a screening process is carried out at this stage, rather than the image acquisition process, and since the fluorescent images sought at this stage are relatively large (an area of about 4 microns instead of 0.2 microns considered for the image acquisition process), a special scanning mode is used, aimed at providing a maximal speed and minimal bleaching, at the expense of image quality. This is achieved by working with a low temperature, low resolution, fast and relatively low image-quality scan. The term "low temperature scan" means that the slide is kept at a low temperature. This may be achieved by cooling the entire capsule space, or by using a local cooling device, like a paltrier, on the slide itself. The use of a low temperature is known for slowing down a physical process. This means that by keeping the slide cold, both the bleaching and the fluorescent processes are slowed down. Operation with a correct temperature provides the system with decreased bleaching and a detectable image. As for low resolution and fast processing, this can be achieved by using CMOS digital camera for the first scanning. This camera provides sufficiently good images in a short time. Using the CMOS camera will enable obtaining lower resolution images at a faster rate, compromising the image quality and increasing speed. Furthermore, the CMOS camera used in the present invention includes hardware capable of performing ROI identification algorithms on-the-fly (in real time). The use of such a set-up, in addition to speeding the identification algorithm by using hardware instead of software, eliminates the need to transfer hundreds of Mega pixel size images to the control unit, in order just to detect whether the scanned field includes any ROI or not. After the hardware identification algorithm is executed on the image, the only data that needs to be transferred to the control unit for further use in the next scan is data indicative of the X, Y, Z coordinates of the detected ROIs.

Now, the second scan is performed. Similarly, using the calibration results and all a priori information entered into the system, all optical parameters and acquiring parameters, are set automatically for the second scan, and in order to optimize the results of the second scan, the calibration results and all a priori information entered to the system are used to set all the environmental parameters (temperature, Oxygen level). For the second scan, a relatively high temperature (10-20°), the same low oxygen level, and dark environment are set. Using the results of the first scan (i.e., the coordinates of all detected ROIs), the route of the scanning process is calculated. This route has to provide the system with the best sequence, which will track all the ROIs detected in the first scan, with minimum bleaching in minimum time. The second scan is aimed at going to the ROIs detected in the first scan, searching for fluorescent signals (labels) containing sub-areas in these regions, and acquiring images of these sub-areas (by illuminating them with suitable exciting light and collecting fluorescent response). To this end, a fine 3-D search in these ROIs is used. Since the fluorescent labels can be very faint and small (about 0.2 microns), optimal conditions should be used for this scanning process, as compared to those of the first scan. Furthermore, this second scanning process includes image acquisition for diagnostic purposes, thus, top-quality images are required. To satisfy these requirements, a top-quality cooled CCD camera is used. The camera is operated at its top performance: no binning and a slow readout. The environmental parameters are also set to give maximum fluorescent signals, even at the expense of bleaching. To achieve this, the slide is heated to provide maximum fluorescence. This process is continued until the number of detected ROIs with signals (with fluorescent labels) reaches a predefined threshold. Thus, the information obtained with the second scan includes images of the detected fluorescent labels containing sub-areas found in the ROIs detected in the first scan, and the X,Y,Z coordinates of the ROIs, where signals were found.

During the above process, the images of the fluorescent signals (labels) and the cell nucleus (or chromosomes) are acquired separately. After all images are acquired, the matching nucleus and signal images are combined to obtain the final color image. Special image enhancement techniques may be used at this stage, to further improve the images. This final set of images is the image set used for further diagnostic purposes by the genetic expert.

The present invention thus provides the optical system and method, consisting of encapsulation of the sample-on-slide and the optical device, build up the fluorescent working station (F-WOS), presenting a complete solution for automatic scanning of biological fluorescent samples. The CEC provides optimal working conditions by encapsulating the sample and the optical device, and preferably also environment sensor(s), which provides for automatically monitoring and controlling environment conditions. One of the advantages of the encapsulation of the F-WOS is that the sample is protected from ambient light in the room, thus bleaching is significantly reduced. The CEC can also provide the sample with an environment free of oxygen, again reducing the bleaching effect significantly. Thus, the CEC provides an environment which enables longer scans of the sample without bleaching. Other environmental hazards such as heat, humidity, radiation, electromagnetic waves, that may also have undesired influence on some biological samples, can also be avoided, when the sample is protected in the CEC. The encapsulation also provides protection of the electronic devices (for example camera), by shielding the electronic devices from electro-magnetic noise in the room. An additional benefit of using the CEC is the significant improvement in signal to noise ratio of the acquired images. This is done by keeping the entire optical system isolated from its surroundings. Thus, ambient light in the room and other electromagnetic noise are shielded from the system. Another important advantage of the CEC, is its ability to protect the operating personal from hazardous condition of the system such as UV light. Additionally, by encapsulating the system, it can be used in any laboratory, without the necessity of providing blackout conditions for the entire laboratory, thus also enabling other people and system operation in the same space with the F-WOS without disturbing each other.

Those skilled in the art will readily appreciate that various modifications and changes can be applied to the embodiment of the invention as hereinbefore exemplified without departing from its scope defined in and by the appended claims.

The invention claimed is:

1. A system for imaging a fluorescently labeled sample, the system comprising a capsule, which is a closable structure made of a material isolating the inside of the capsule from its surrounding environment, and which has a support stage for receiving the sample and carrying it thereinside during the imaging; and an optical device at least partly accommodated inside the capsule and operable to illuminate the sample with incident radiation to excite a fluorescent response of the sample, detect the fluorescent response, and generate data indicative thereof;

wherein said optical device comprises a light source system, an image formation system, and light directing/collecting optics having an objective lens arrangement and defining illumination and detection channels of light propagation;

wherein the image formation system comprises a detector arrangement;

wherein said detector arrangement has at least two different detectors;

wherein the detector arrangement comprises the first detector operable to perform a relatively fast scan of the sample to real-time identify at least one pre-defined region of interest in the sample and to process the fluorescent response to thereby produce data indicative of coordinates of the region of interest, and the second detector operable to provide data indicative of an image of a fluorescent labels containing sub-area of the region of interest with an image quality enabling data analysis and image acquisition.

2. The system according to claim 1, wherein each of the first and second detectors is a CMOS or CCD camera.

3. The system according to claim 2, wherein the first detector is the CMOS camera, and the second detector is the cooled CCD camera.

4. The system according to claim 1, comprising a scanning system operable to enable three-dimensional scanning of the sample.

5. The system according to claim 4, wherein said scanning system comprises a support stage for supporting the sample in the capsule, and a drive operable for driving a movement of the stage with respect to an inspection plane.

6. The system according to claim 5, wherein the stage is movable within the inspection plane and a long an axis perpendicular to the inspection plane.

7. The system according to claim 1, comprising a control unit connectable to the optical device to operate it, to process and analyze data indicative of the image of the sample, and produce inspection results.

8. The system according to claim 7, wherein said control unit is responsive to the data generated by the sensor arrangement to operate inlet and outlet channels to adjust said at least one environment condition inside the capsule.

9. The system according to claim 7, comprising a communication means between the capsule and the control unit for providing a continuous flow of data between them, said communication means enabling storage of data indicative of the acquired images in a database utility.

10. The system according to claim 9, wherein said database utility is a part of the control unit.

11. The system according to claim 9, wherein said database utility is located in an external device connectable to the control unit.

12. The system according to claim 7, wherein said control unit comprises a data processing and analyzing utility preprogrammed to process the data indicative of the detected fluorescent response to carry out at least one of the following: locating the at least one predefined region of interest, focusing on the located region, analyzing the image of the region of interest, selecting at least one sub-area in the region of interest for further image acquisition and analysis, calculating at least one optimal parameter for acquiring different images and providing diagnosis evaluation based on the acquired images and predefined statistics.

13. The system according to claim 12, wherein said at least one optimal parameter includes at least one of the following sample's parameters: roundness of the region of interest, overlapping between adjacent regions of interest, and size of the region of interest.

14. The system according to claim 9, wherein the database utility is preprogrammed to carry out at least one of the following operations: saving the acquired image, conducting search algorithms on the database, and allowing adding of new fields of data to each item in the database.

15. A method of imaging a fluorescently labeled sample utilizing the system for imaging a fluorescently labeled sample, the system comprising:

a capsule, which is a closable structure made of a material isolating the inside of the capsule from surrounding environment, the capsule comprising a support stage for receiving the sample and carrying it thereinside during the imaging process in a manner enabling displacement of the sample with respect to an inspection plane, and having inlet and output channels operable to affect environment conditions inside the capsule;

an optical device at least partly accommodated inside the capsule and operable to illuminate the sample with incident exciting radiation to excite a fluorescent response of the sample, detect the fluorescent response, and generate data indicative thereof;

a sensor arrangement accommodated inside the capsule and operable to detect at least one of the following environment conditions inside the capsule: temperature, light intensity, electromagnetic radiation intensity, content of at least one gas in the capsule, and humidity; and to generate data indicative thereof; and a control unit connectable to the capsule and response to said data indicative of the detected fluorescent response to output an image of the illuminated region of the sample, responsive to said data indicative of the at least one environment condition to operate the inlet and output channels of the capsule so as to provide a desired environment condition inside the capsule, the method comprising:

(i) first scanning of the sample to detect regions of interest in the sample and determine coordinates of the detected regions of interest;

(ii) utilizing the results of the first scanning, and performing second scanning of the regions of interest to detect sub-areas of the regions of interest containing the fluorescent labels and acquire images of said sub-areas.

16. The method according to claim 15, wherein the light environment inside the capsule is 0.001 lux or less.

17. The method according to claim 15, wherein the first and second scanning are carried out at low oxygen level in the capsule as compared to that of the environment outside the capsule.

18. The method according to claim 15, wherein the first scanning is carried out at relatively low temperature inside the capsule as compared to that of the second scanning.

19. The method according to claim 18, wherein the temperature of the first scanning is about 2-8° C.

20. The method according to claim 18, wherein the temperature for the second scanning is about 10-20° C.

21. The method according to claim 15, comprising:

upon loading the fluorescently labeled sample into the capsule, and prior to starting the first scanning, setting the sample's type and performing a calibration process to select at least one optimal parameter for the imaging process;

utilizing the calibration results to automatically set optical parameters of the system prior to each of the first and second scanning process and for the second scanning.

22. The method according to claim 21, wherein said calibration process includes acquiring a set of images of the sample under different conditions inside the capsule.

23. The method according to claim 22, wherein said different conditions include at least one of the following: light intensity, the type of a spectral filter to be used in the optical device, and a position of the sample with respect to the optical device.

24. The method according to claim 21, wherein said at least one optimal parameter is the optimal light source intensity value and is determined as the intensity corresponding to an optimum between a maximum fluorescent emission of the sample obtained at a minimum bleaching.

25. The method according to claim 15, wherein the first scanning process utilizes a CMOS camera detector of the image formation system, and the second scanning process utilizes a CCD camera detector of the image formation system.

* * * * *

UNITED STATES PATENT AND TRADEMARK OFFICE
CERTIFICATE OF CORRECTION

PATENT NO.       : 7,326,938 B2
APPLICATION NO.  : 10/487441
DATED            : February 5, 2008
INVENTOR(S)      : Palti-Wasserman et al.

It is certified that error appears in the above-identified patent and that said Letters Patent is hereby corrected as shown below:

At claim 8, at column 13, line 32, after the word "operate" insert --said--.

Signed and Sealed this

Fifteenth Day of June, 2010

David J. Kappos
*Director of the United States Patent and Trademark Office*